US010751489B2

(12) United States Patent
Hadash et al.

(10) Patent No.: US 10,751,489 B2
(45) Date of Patent: Aug. 25, 2020

(54) DEVICE AND METHOD FOR ADMINISTERING MEDICAMENTS TO THE BRAIN

(71) Applicant: Inhaletech LLC, Minneapolis, MN (US)

(72) Inventors: Joseph Hadash, Lapid (IL); Yair Hadash, Lapid (IL)

(73) Assignee: Inhaletech LLC, Minneapolis, MN (US)

( * ) Notice: Subject to any disclaimer, the term of this patent is extended or adjusted under 35 U.S.C. 154(b) by 709 days.

(21) Appl. No.: 15/312,011

(22) PCT Filed: May 18, 2015

(86) PCT No.: PCT/IL2015/050527
§ 371 (c)(1),
(2) Date: Nov. 17, 2016

(87) PCT Pub. No.: WO2015/177788
PCT Pub. Date: Nov. 26, 2015

(65) Prior Publication Data
US 2017/0072145 A1  Mar. 16, 2017

Related U.S. Application Data

(60) Provisional application No. 61/996,922, filed on May 19, 2014.

(51) Int. Cl.
| *A61M 15/00* | (2006.01) |
| *A61M 16/06* | (2006.01) |
| *A61M 15/08* | (2006.01) |
| *A61M 16/00* | (2006.01) |

(52) U.S. Cl.
CPC .......... *A61M 15/009* (2013.01); *A61M 15/08* (2013.01); *A61M 16/0666* (2013.01);
(Continued)

(58) Field of Classification Search
CPC ............ A61M 15/009; A61M 16/0666; A61M 2016/0018; A61M 2205/3375;
(Continued)

(56) References Cited

U.S. PATENT DOCUMENTS

| 8,639,288 B1* | 1/2014 | Friedman ................ A61M 5/20 455/556.1 |
| 2004/0231667 A1* | 11/2004 | Horton .............. A61M 15/0065 128/202.13 |

(Continued)

FOREIGN PATENT DOCUMENTS

| WO | WO 2009/100383 A2 | 8/2009 |
| WO | WO 2013/128447 A1 | 9/2013 |

OTHER PUBLICATIONS

Patent Cooperation Treaty, International Search Report, International Patent Application No. PCT/IL2015/050527, dated Aug. 30, 2015, 5 Pages.

(Continued)

*Primary Examiner* — Jason E Flick
*Assistant Examiner* — Dung T Ulsh
(74) *Attorney, Agent, or Firm* — Fenwick & West LLP (57) ABSTRACT

The present invention provides a system for administering a therapeutic substance to a brain, for example a brain of a person afflicted by a neurodegenerative disorder. The system may include communicating with the person and locating it via a smartphone, characterizing the level of its alertness or cognitive abilities, and initiating the substance release via a vocal signal. The system enables to bypass the blood brain barrier while also reducing undesired systemic concentration peaks of the substance.

21 Claims, 13 Drawing Sheets

(52) U.S. Cl.
CPC ............... *A61M 2016/0018* (2013.01); *A61M 2016/0021* (2013.01); *A61M 2205/3375* (2013.01); *A61M 2205/3569* (2013.01); *A61M 2205/3592* (2013.01); *A61M 2205/52* (2013.01); *A61M 2205/80* (2013.01); *A61M 2205/8206* (2013.01); *A61M 2210/0618* (2013.01); *A61M 2210/0693* (2013.01)

(58) Field of Classification Search
CPC .. A61M 2205/3569; A61M 2205/3592; A61M 2205/52; A61M 2205/80; A61M 2205/8206; A61M 2210/0618; A61M 2210/0693; A61M 2016/0021
See application file for complete search history.

(56) References Cited

U.S. PATENT DOCUMENTS

| | | | |
|---|---|---|---|
| 2006/0107957 A1* | 5/2006 | Djupesland | A61M 15/08 128/206.11 |
| 2006/0130832 A1 | 6/2006 | Schechter et al. | |
| 2007/0193582 A1* | 8/2007 | Kwok | A61M 16/00 128/204.18 |
| 2012/0190001 A1* | 7/2012 | Knight | G09B 7/00 434/362 |
| 2012/0277716 A1* | 11/2012 | Ali | G06F 19/3468 604/500 |
| 2013/0275139 A1* | 10/2013 | Coleman | A61M 16/0672 704/275 |
| 2014/0014104 A1 | 1/2014 | Hoekman et al. | |
| 2014/0073562 A1* | 3/2014 | Djupesland | A61M 15/08 514/4.8 |

OTHER PUBLICATIONS

Patent Cooperation Treaty, Written Opinion of the International Searching Authority, International Patent Application No. PCT/IL2015/050527, dated Aug. 30, 2015, 7 Pages.

Extended European search report, European Patent Application No. 15796873.6, dated Jan. 4, 2018, 6 pages.

* cited by examiner

DEVICE AND METHOD FOR ADMINISTERING MEDICAMENTS TO THE BRAIN

RELATED APPLICATIONS

This application is a 35 U.S.C. 371 national stage filing of International Application No. PCT/IL2015/050527, filed on May 18, 2015, which claims the benefit of U.S. Provisional Application No. 61/996,922 filed May 19, 2014, the disclosures of which are hereby incorporated by reference.

FIELD OF THE INVENTION

The present invention relates to a device and a method for delivering substances to the brain, while bypassing the blood brain barrier and reducing undesired systemic concentration peaks of the substances.

BACKGROUND OF THE INVENTION

Most drugs do not enter the brain through the blood stream due to the neuro-protective mechanism known as the blood brain barrier [The Merck Manual of Diagnosis and Therapy, 1999, 17th Ed., page 2562]. It has been shown that drugs administered as nose drops can enter the brain directly without entering the blood stream; however, none of the considered drug-targeting strategies for bypassing the blood brain barrier (BBB) have been proved sufficiently effective, and the dangerous side effects due to systemic overdose have been difficult to control [for example see Miyake M. M. and Bleier B. S.: Am. J. Rhinol. Allergy, 2015, 29(2), 124-7]. The direct path from the nasal cavity to the brain along the olfactory nerves was considered, for example, for intranasal delivery of insulin for the patients suffering from Alzheimer's disease, as intranasal insulin was shown to improve memory, attention, and functional status in patients in the early stages of Alzheimer's disease and those with mild cognitive impairment; however, any systemic insulin increase can have sever effects and must be, therefore, strictly prevented [Hanson L. R. and Frey W. H.: BMC Neurosci. 2008, 9 (Suppl 3): S5]. A need is felt for drug delivery systems for administering medicaments to the brain without dangerous changes of the systemic drug levels. Particularly, a need is felt for drug delivery systems for patients suffering from disorders associated with the central nervous system (CNS), wherein the disorders limit the capabilities of the patients to fully cooperate during the process of administering the drugs. Only in the U.S. there are more than five million people suffering from the Alzheimer's disease. It is therefore an object of the invention to provide a system for delivering medicaments to the brain of a human subject that suffers from a CNS disorder.

It is another object of the invention to provide a drug delivery system for administering a medicament to a subject while bypassing the BBB.

It is a further object of the invention to provide a device and a method for administering a medicament to a subject, while precluding dangerous systemic concentrations of said medicament.

It is a still further object of the invention to provide a device and a method for delivering a substance to the brain of a subject while precluding undesired increases of the substance concentrations in the blood or plasma of said subject.

It is also an object of the invention to provide a device and a method for administering a medicament to a subject suffering from a condition selected from neurologic disorders and psychiatric disorders, while precluding systemic overdose of said medicament.

It is still another object of the invention to provide a device and a method for administering a medicament to a subject with lowered level of alertness or reduced cognitive abilities.

It is further an object of the invention to provide a drug delivery system for administering a medicament to a subject comprising processing parameters associated with the level of alertness or the cognitive abilities of said subject.

Other objects and advantages of present invention will appear as description proceeds.

SUMMARY OF THE INVENTION

This invention provides a device for delivering a dose of a substance to the brain of a subject while bypassing the blood brain barrier, comprising i) a canister for holding a liquid comprising said substance; ii) a voice sensor configured to generate an electrical signal within a portion of the device in response to a vocal signal; iii) a processor configured to receive said electrical signal as a command for either starting a motor or blocking the motor; iv) a valve associated with said motor and configured to release a part of said dose into nasal cavities of said subject when the motor is started, wherein the substance is pumped from said canister in the form of solution or suspension and released into said cavities in the form of aerosol; v) an integrator for registering the total quantity of the released substance; wherein said substance passes through said nasal cavities via ethmoid bone to the brain of the subject, and wherein said dose is divided into a plurality of said predetermined parts to reduce the peak tissue concentrations and/or peak systemic concentrations of said substance. In some embodiments of the invention, said integrator may be incorporated within said processor. Said vocal signal may be a speech of said subject or of attending personnel. Said vocal signal may be a certain word or a certain word sequence. In one embodiment, said vocal signal is a speech of said subject who starts the motor and initiates the release of a part of said dose to its nostrils when such release is required. In another embodiment, said vocal signal is a speech of said personnel who either starts the motor when the release of the medicament is required or blocks the motor when the release of the medicament is not required or is undesired. In a preferred embodiment of the invention, provided is a device for delivering a daily dose of a medicament to the brain of a subject while bypassing the blood brain barrier, comprising i) a canister for holding a solution or suspension of said medicament; ii) a voice sensor configured to generate an electrical signal within a portion of the device in response to speech of the subject; iii) a processor configured to receive said electrical signal as a command for starting a motor; iv) a valve associated with said motor and configured to release a part of said dose in the form of medicament aerosol into nasal cavities of said subject when the motor is started; v) an integrator for registering the total quantity of the released medicament; wherein said medicament passes through said nasal cavities via ethmoid bone to the brain of the subject, and wherein said daily dose is divided into a plurality of said predetermined parts to reduce the peak tissue concentrations and/or peak systemic concentrations of said medicament. The device according to the invention preferably comprises a loudspeaker enabling the subject to hear attending personnel or family members who may affect the subject or give vocal commands. The processor in one embodiment of the device according to the invention further records the speech of said subject when said subject responds to questions aimed at characterizing the level of alertness or cognitive abilities of the subject. Said processor may further provide cognitive parameters corresponding to the reactions of said subject to the questions. In a preferred embodiment of the invention, the size of the dose or of it's a part thereof in said device is affected by the cognitive parameters provided by said processor. Said sensor in the device of the invention may comprise a smartphone, or may be associated with a smartphone, which connects the subject with attending personnel or family members. Said smartphone preferably comprises GPS and enables to locate the subject.

The substance delivered by the device of the invention is preferably a medicament for treating or preventing a condition selected from neurologic or psychiatric disorders. Examples of the neurologic disorders are pain, headache, dementia, seizure disorders, and others, including migraine, Alzheimer's diseases, Parkinson diseases, epilepsy, and others. Examples of the psychiatric disorders include anxiety disorders, mood disorders, schizophrenia, drug dependence, and others. The device according to the invention for delivering a dose of the medicament for treating or preventing said condition to the brain of the subject while bypassing the blood brain barrier usually comprises i) a canister for holding a of solution or suspension of said medicament; ii) a voice sensor configured to generate an electrical signal within a portion of the device in response to speech of the subject; iii) a processor configured to receive said electrical signal as a command for starting a motor; iv) a valve associated with said motor and configured to release a part of said dose in the form of aerosol into nasal cavities of said subject when the motor is started; and v) an integrator for registering the total quantity of the released medicament; wherein said speech results in moving the soft palate of the subject and in naturally separating the nasal cavities from the airways and limits the quantity of the medicament which enters to the blood system. In a preferred embodiment of the invention, the device delivers a substance which is a medicament for treating a neurodegenerative disorder. In one preferred embodiment, said substance is insulin and said neurodegenerative disorder is Alzheimer's disease.

The invention is directed to a method for delivering a dose of a substance to the brain of a subject while bypassing the blood brain barrier, comprising i) generating an electrical signal in response to a vocal signal by a voice sensor; processing said electrical signal by a processor; ii) activating by said processor a motor associated with a valve configured to release a part of said dose of said substance into nasal cavities of said subject when the motor is started; iii) releasing said part of the dose in the form of aerosol, wherein said substance is pumped from a canister where it is in the form of solution or suspension; and iv) registering the total quantity of the substance released during certain period; wherein said substance passes through said nasal cavities via ethmoid bone to the brain of the subject, and wherein said dose is divided into a plurality of said predetermined parts to reduce the peak tissue concentrations and/or peak systemic concentrations of said substance. Said vocal signal is preferably a speech of said subject or of attending personnel. The method of the invention preferably further comprises recording the speech of said subject when responding to questions aimed at characterizing the level of alertness or cognitive abilities of the subject. In a preferred embodiment, the method of the invention comprises a step of characterizing the level of alertness or cognitive abilities of the subject. The method preferably comprises providing cognitive parameters of said subject. In a preferred embodiment, the sensor in the method of the invention comprises a smartphone which connects the subject with attending personnel or family members. The method preferably comprises locating the subject by a GPS associated with the smartphone. Said substance in the method of the invention is preferably a medicament for treating or preventing a condition selected from neurologic or psychiatric disorders. In a preferred embodiment of the method according to the invention, said speech results in moving the soft palate of the subject, thereby naturally separating the nasal cavities from the airways and limiting the quantity of the medicament which enters to the blood system of the subject. Said substance is preferably a medicament for treating Alzheimer's disease, such as insulin.

The invention provides a system for delivering a dose of a substance to the brain of a subject while bypassing the blood brain barrier, comprising i) a canister for holding a liquid comprising said substance; ii) a voice sensor configured to generate an electrical signal within a portion of the device in response to a vocal signal; iii) a processor configured to receive said electrical signal as a command for either starting a motor or blocking the motor; iv) a valve associated with said motor and configured to release a part of said dose into nasal cavities of said subject when the motor is started, wherein the substance is pumped from said canister in the form of solution or suspension and released into said cavities in the form of aerosol; and v) an integrator for registering the total quantity of the released substance; wherein said substance passes through said nasal cavities via ethmoid bone to the brain of the subject, and wherein said dose is divided into a plurality of said predetermined parts to reduce the peak tissue concentrations and/or peak systemic concentrations of said substance. The system preferably comprises also a loudspeaker enabling the subject to hear attending personnel or family members who may affect the subject or give vocal commands. In a preferred embodiment, the system of the invention further comprises a smartphone which connects the subject with attending personnel or family members. The system preferably further comprises GPS for locating said subject. In a preferred embodiment, the system delivers a medicament for treating or preventing a condition selected from neurologic or psychiatric disorders.

BRIEF DESCRIPTION OF THE DRAWINGS

The above and other characteristics and advantages of the invention will be more readily apparent through the following examples, and with reference to the appended drawings, wherein:

FIG. 1. is a conceptual drawing illustrating a system according to one embodiment of the invention that includes an intranasal medication delivery device (IMDD) and a computing device in relation to a user;

FIG. 2. is a conceptual drawing illustrating a device according to FIG. 1 with a back side maintenance door;

FIG. 3. is a conceptual drawing illustrating an IMDD according to one embodiment of the invention;

FIG. 4. is another conceptual drawing illustrating an example IMDD according to one embodiment of the invention;

FIG. 5. is a still another conceptual drawing illustrating an example IMDD according to one embodiment of the invention;

FIG. 6. to FIG. 8 are a flow of computing device screens representing an example of a process for delivering sub-doses (pulses) of medication according to one embodiment of the invention, comprising IMDD detecting speech via a voice sensor (microphone);

DETAILED DESCRIPTION OF THE INVENTION

A drug delivery system has now been provided which enables to deliver a substance to the brain of a subject while keeping a relatively low systemic concentration of said substance. The invention relates to medical devices and, more particularly, to the delivery of intranasal content by medical devices. The invention also relates to a drug delivery system comprising collecting clinical and/or cognitive data of the user. Since drugs administered as nose aerosols can advantageously enter the brain directly without entering the blood stream, via olfactory nerves passing from the nasal cavity to the brain via ethmoid bone, potentially new solutions to the old problem of bypassing the BBB appear; however, there are factors which limit the simple utilization of this phenomenon, including escape of the delivered medicament to other body parts, resulting in an undesired systemic concentration of the medicament. For example, it is known that it is difficult to treat patients with insulin without causing side effects. The present invention addresses this problem by efficient dosing the aerosolized drug to the patient suffering from Alzheimer's diseases in certain time intervals, in accordance with the instant state of the patient, characterized, in one embodiment, also by means of the cognitive parameters collected in the system. The system of the invention may comprise and employ cognitive tests. In a system according to the invention, the drugs are delivered from the container to the nose and to the brain while using nose aerosols or nasal sprays. In a preferred embodiment of the invention, the nasal delivery system comprises atomized pump. In one preferred embodiment, the system of the invention delivers intranasal insulin to the brain without causing the unwanted side effects in sub-doses determined by the system in accordance with parameters comprising the instant state of the patient, the mental state of the patient, the level of alertness of the patient, the instant cognitive abilities of the patient, and the total daily predetermined dose. The system according to the invention may be employed for administering medicaments to patients suffering from other CNS conditions, including neurodegenerative disorders, via nasal drug delivery systems without losses of the dosage into other parts of the body, such as to the respiratory tract including lungs; for example, the system of the invention may be employed for delivering growth factors or nerve growth factors to the brain afflicted with Parkinson's disease.

Generally, the invention relates to techniques and systems for controlling the release of a substance into a patient nostrils. For example, an intranasal medication dosing device (IMDD) may be configured to trigger the release of at least a portion of a dose of medication in response to words spoken by a patient. The IMDD may include a vocal sensor (microphone) that generates a signal; the signal may comprise an air flow through a processor element caused by a speaking action of the patient. In response to a command based on the signal indicative the speech, the IMDD may control a motor pushing a canister effecting the valve to open and release at least a portion of a dose of medication stored in the canister coupled to the PMDD. In some examples, the IMDD may include processors and/or modules to generate the command such that the IMDD is configured to operate individually. In other examples, a computing device (e.g., a mobile computing device such as a smartphone, tablet computer, notebook computer, or portable medical device) may generate the command for controlling the electrical motors to push the canister and let the valve to release the medication. The smartphone also enables a constant communication line between the patient and the nursing personnel, wherein the line may be always opened and used by either of them. The communication can be initiated by simply pushing a button or by emitting/generating a voice signal. The IMDD may transmit the signal indicative of the patient speech to the computing device, the computing device may generate the command for controlling the pushing motor and the valve, and the computing device may subsequently transmit the command to the IMDD for controlling the delivery of the medication from a canister coupled to the IMDD. By offloading at least some of the processing functions to the computing device, the IMDD may benefit from additional functionality of the computing device and be manufactured at a reduced cost. In other example, the accumulation of Mini-mental state exam (MMSE)/Mini-cog exam answers/results, or accumulating of clinical data can be analyzed and transferred to central data collecting system. Questionnaires for assessing the state of mind, or degree of dementia, and diaries including quantities/times, as well as detailed programs for drug delivery may be advantageously employed. In one example, the invention provides a method that includes generating a signal indicative of speech within a processor device, receiving, by a processor, a command based on the signal and associated with a motor pushing the canister valve configured to at least partially control release of a medication via the attached nostrils of the device (or nostril tips or nostril insertions), and controlling, by the processor and based on the received command, the motor pushing and releasing the canister valve to release at least a portion of a dose of the medication into the attached nostrils. In another example, the disclosure describes a intranasal medication dosing device including a valve configured to at least partially control release of medication, a vocal sensor configured to generate a signal indicative of speech within a processor, and the processor configured to receive a command based on the signal and associated with the valve and control, based on the received command, the valve to release at least a portion of a dose of the medication into the attached nostrils. In another example, the disclosure describes a system including a housing configured to accept a medication canister containing a medication, a dispensing portion coupled to the housing, a valve configured to at least partially control release of medication from the medication canister, a inhaling sensor configured to generate a signal indicative of inhaled air flow within respiratory system, and a processor configured to receive a command based on the signal and associated with the valve, and control, based on the received command, the valve to release at least a portion of a dose of the medication into the nostrils within the dispensing device. In another example, the disclosure describes a computer-readable storage medium comprising instructions that, when executed by one or more processors of a computing device, cause the one or more processors to receive data indicative of inhaling air flow within the user respiratory system, responsive to receiving the data, generate, based on the received data, a command associated with a valve configured to at least partially control release of a medication via the intranasal medication dosing device, and wherein the command indicates one of an open configuration or a closed configuration of the valve, and transmit the command to a communication unit associated with the intranasal medication dosing device. Examples of several aspects of the invention are set forth in the accompanying drawings and the description below. Other features, objects, and advantages will be apparent from the description and drawings, and from the claims.

This invention provides various techniques and systems for controlling the release of a substance into nostrils of the patient, particularly a patient suffering from a neurological or psychiatric diseases, for example a neurodegenerative diseases. Typically, patients requiring nasal medications to treat various disorders and conditions may rely upon nasal delivery devices to obtain the prescribed medication. In one embodiment, the patient attempts to coordinate an inhaled breath with manual handling of a medication container or nasal device. The invention particularly aims at delivering substance in response to detecting a vocal signal, such as speech. For example, a patient may use an IMDD to receive substance directed to the olfactory mucosa.

Figure 1:
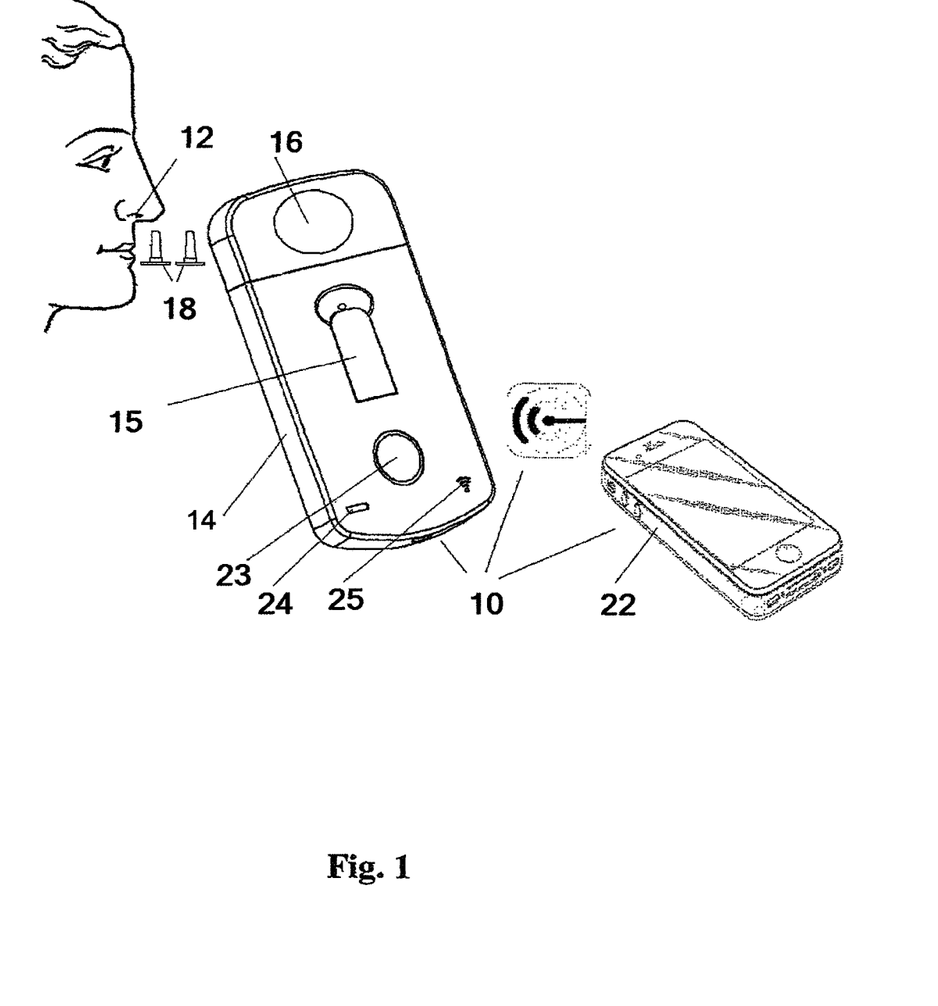
Figure 2:
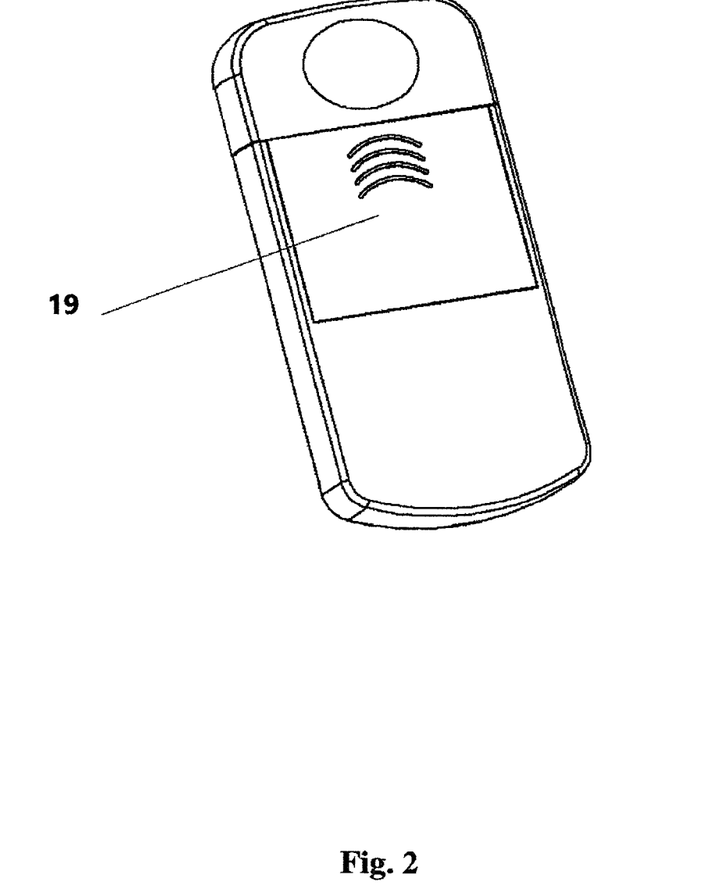
Figure 3:
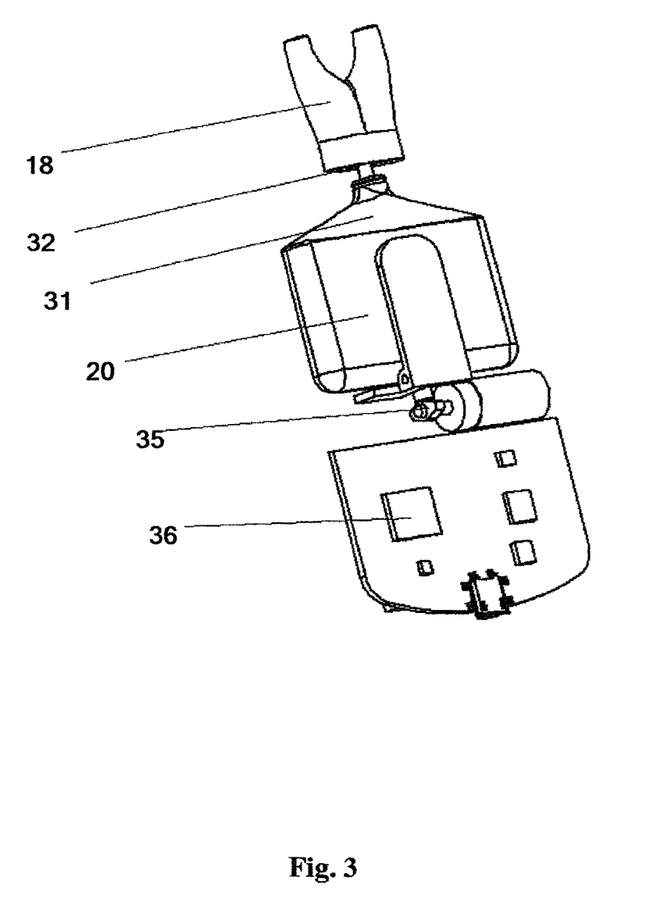
Figure 4:
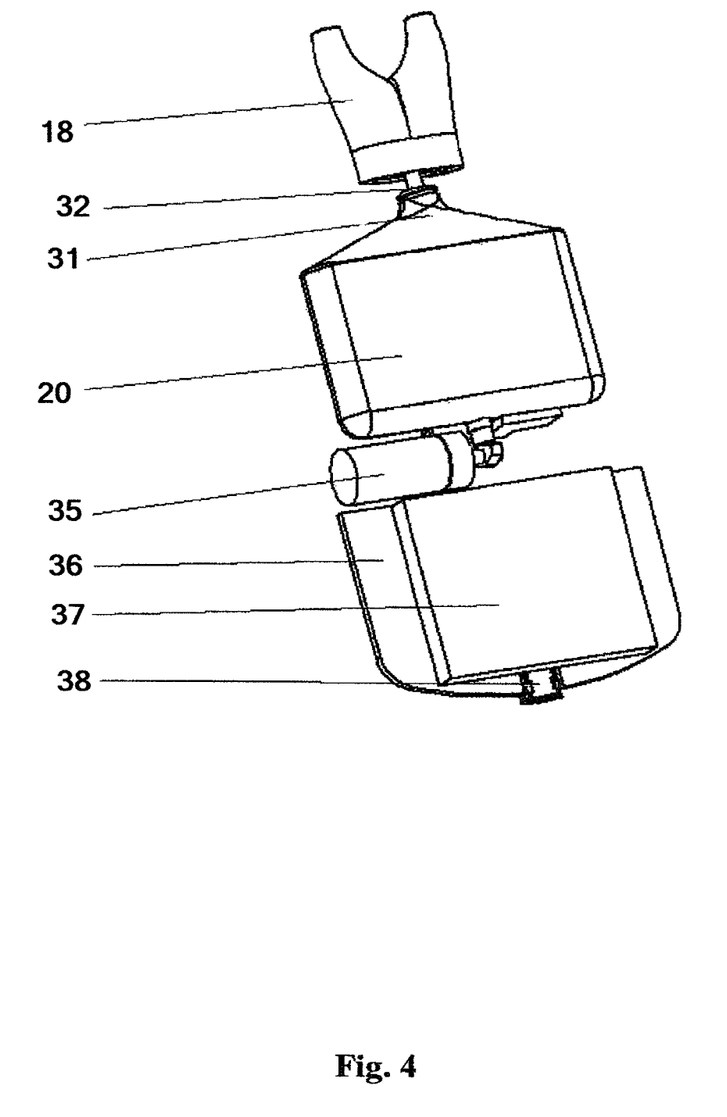
Figure 5:
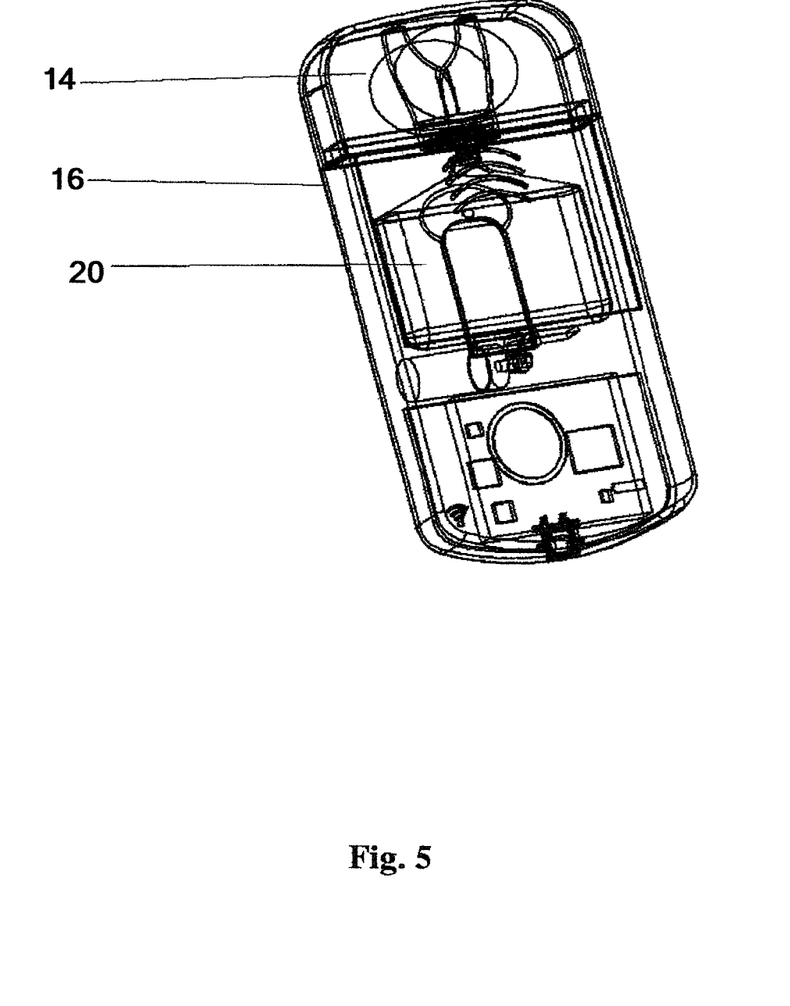
Figure 6:
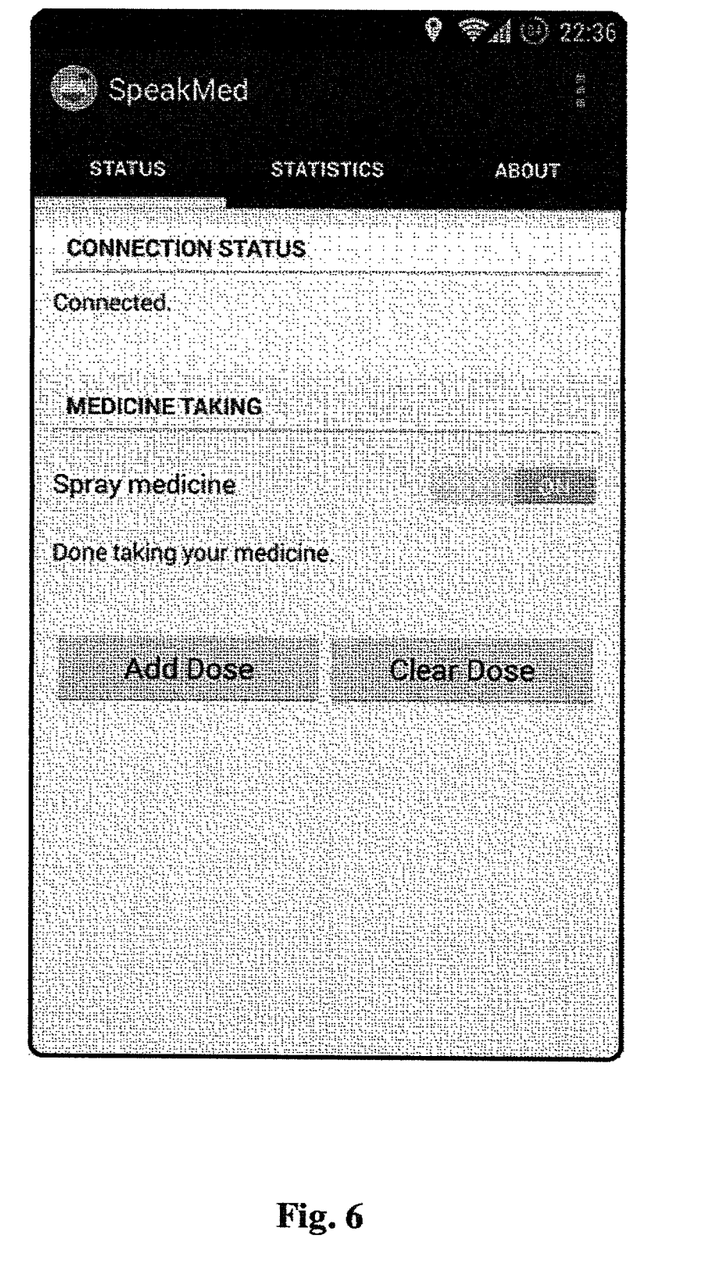
Figure 7:
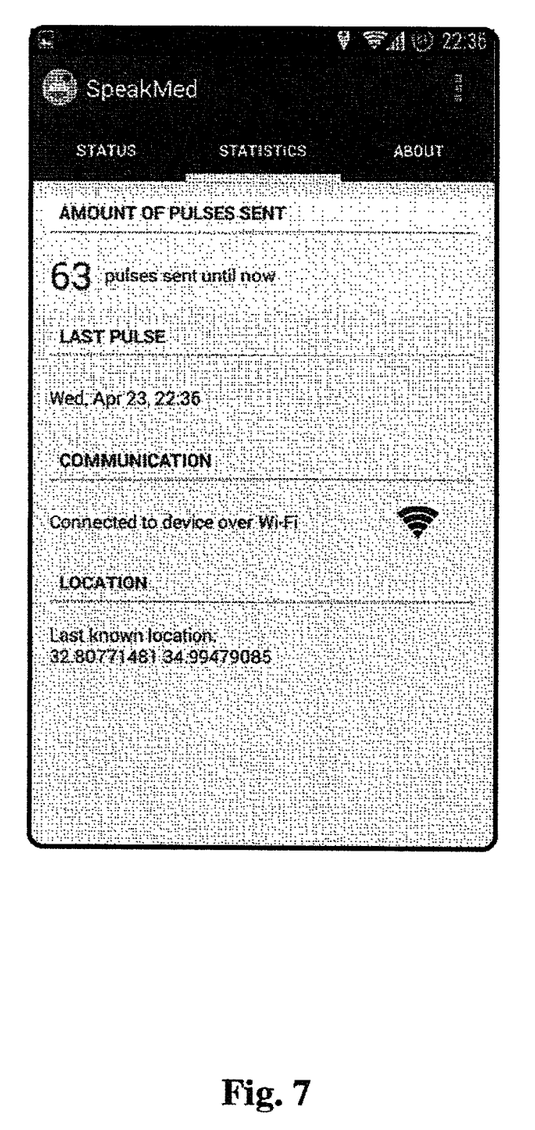
Figure 8:
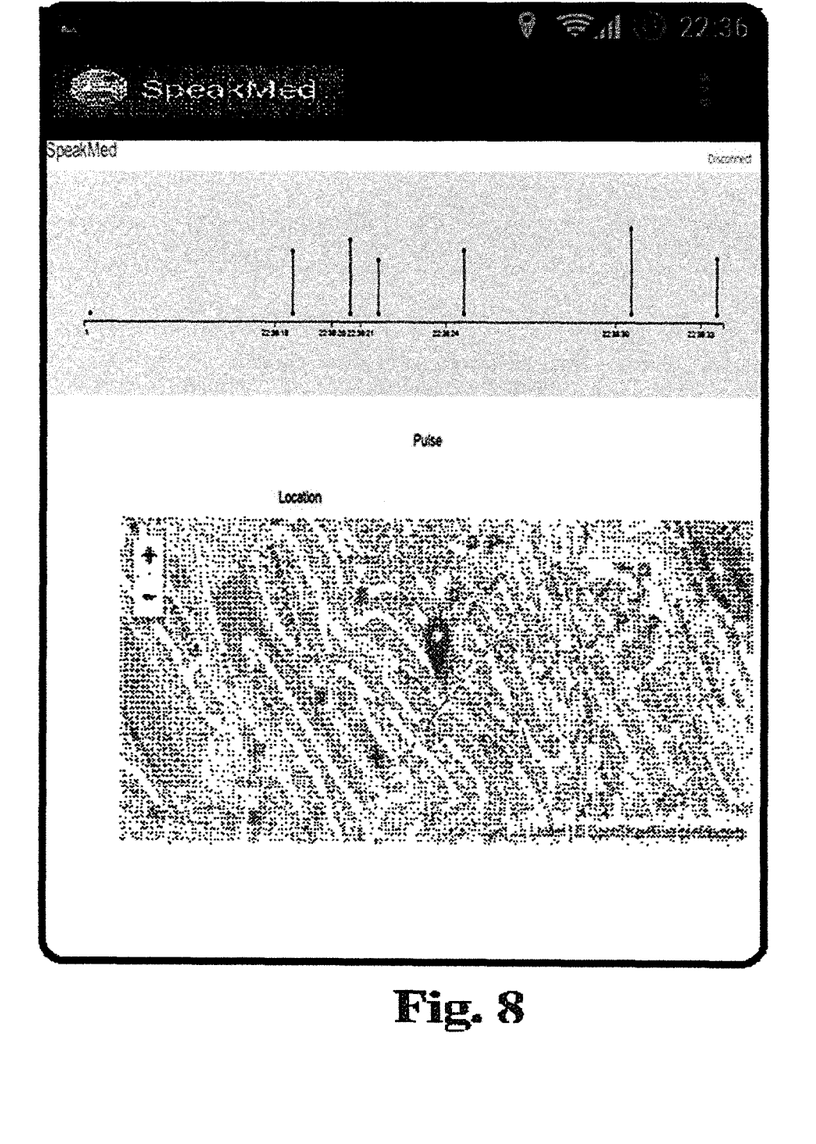
Figure 9:
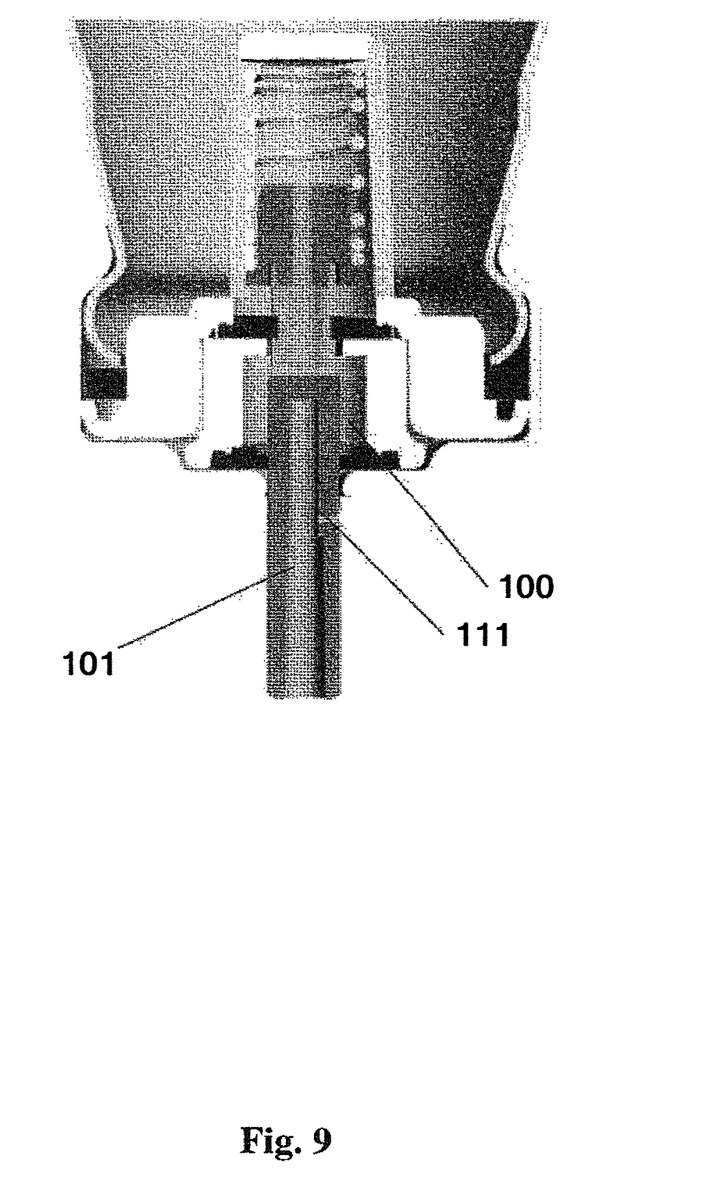
FIG. 9 to FIG. 11 are conceptual drawings illustrating an example valve within a metered dose compartment of an IMDD according to one embodiment of the invention; closing of the valve of the device, followed by opening and closing again, are visualized in the drawings.
Figure 10:
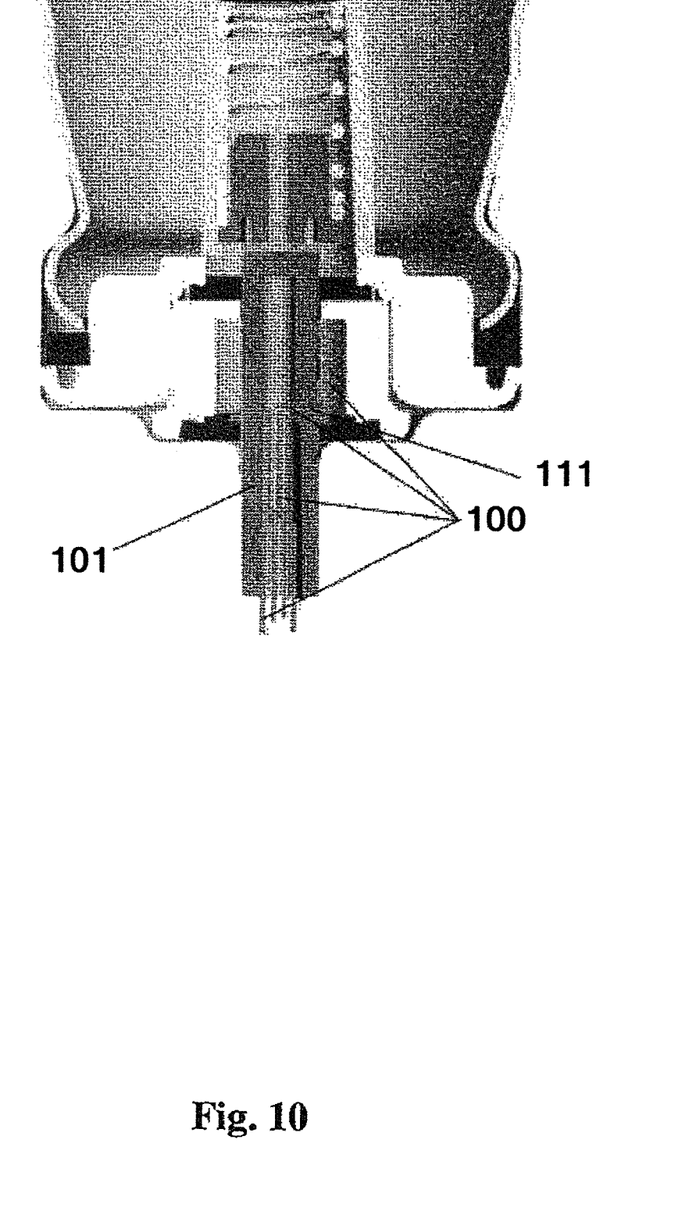
Figure 11:
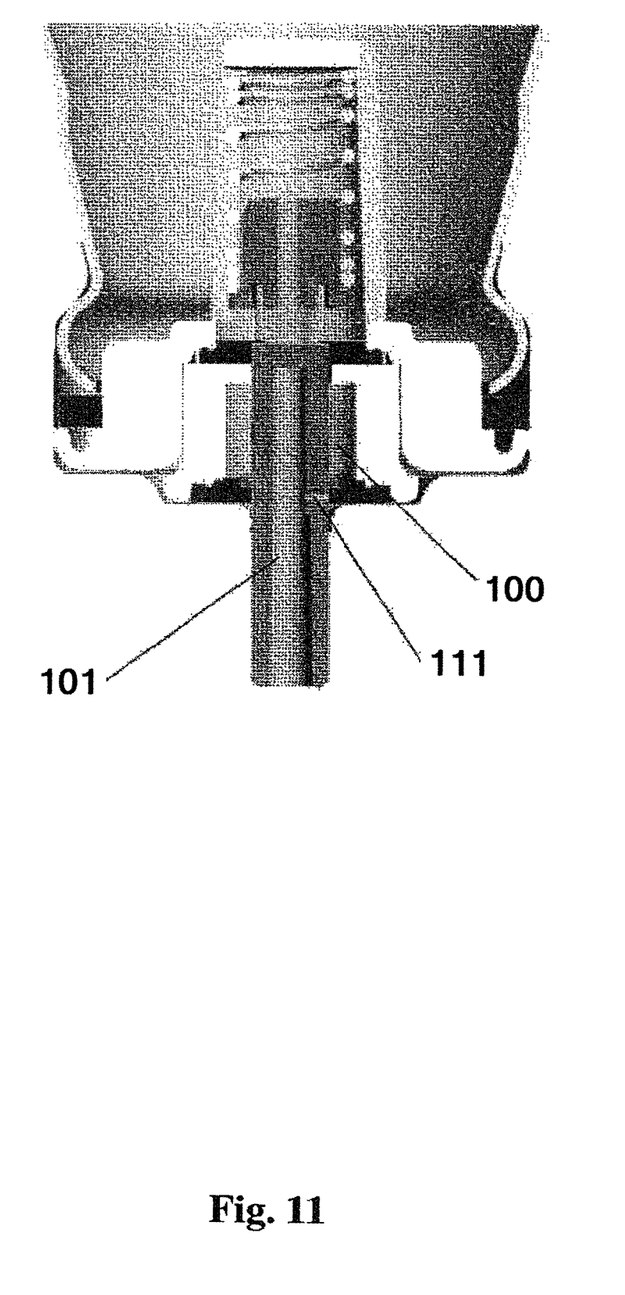
Figure 12:
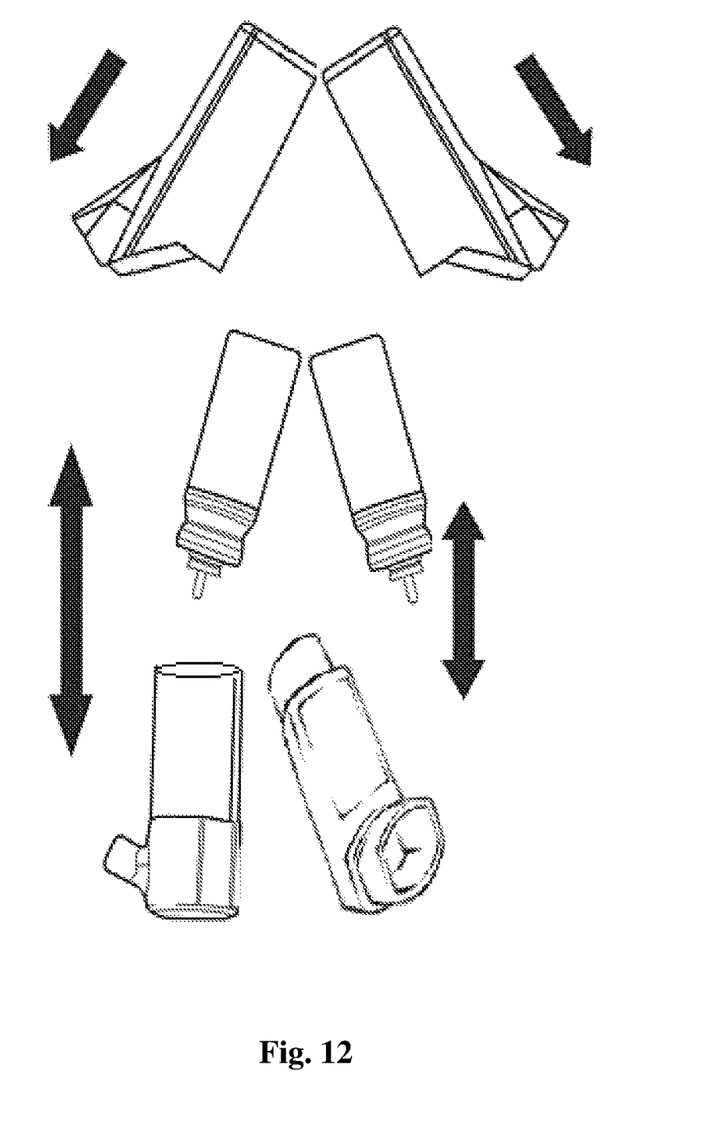
FIG. 12 is a scheme illustrating an existing manufactured aerosol spray device (MDI-actuated with flow sensor), and Precision Olfactory Delivery (POD) device or Nasal Metered Dose Inhaler (MDI)—to be incorporated into a device (add on) in one embodiment of the invention.
Figure 13:
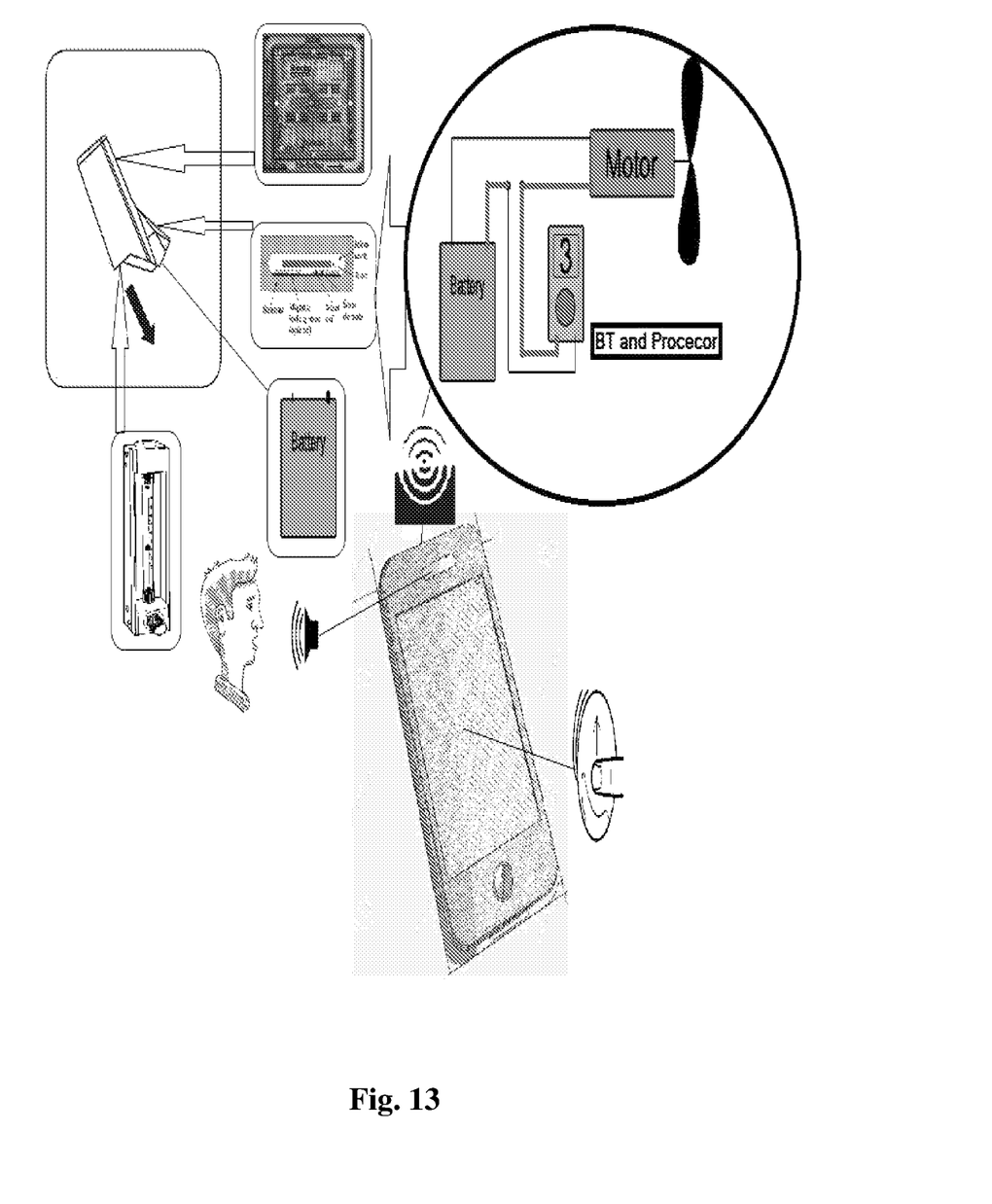
FIG. 13 is a conceptual drawing illustrating a system including the motor, BT+processor+sensor, and battery, according to one embodiment of the invention, including the commercial aerosol device as shown in FIG. 12 and a computing device in relation to a user.

Some embodiments of the invention are schematically related to in the attached drawings. FIG. 1 is a conceptual drawing illustrating an example system 10 that includes intranasal medication delivery device (IMDD) 14 and computing device 22 in relation to user 12. IMDD 14 may include a nozzle tips 18 and housing 16, and a handle for manual operation 15, and a switch for manual/electrical operation 23, and an indicator for power 24, and an indicator for communication 25, Nozzle tips 18 may be removably attached to housing 16, permanently coupled to housing 16, or formed with housing 16. FIG. 2 is a conceptual drawing illustrating an example of the back side of the intranasal medication delivery device (IMDD) 14 that includes a sliding panel 19. FIG. 3 the housing may be configured to accept canister 20 wherein the canister includes metered dose valve 31 a orifice 32 and nozzle tip 18 in the end, on the anther end it is the electro mechanical motor 35 connected to the canister, and a communication and control circuit 36. FIG. 4 is the housing which may be configured to accept canister 20 wherein the canister includes metered dose valve 31 a orifice 32 and nozzle tip 18 in the end, on the anther end it is the electro mechanical motor 35 connected to the canister, and a communication and control circuit 36, and power supply reservoir 37 and a power charger 38. FIG. 5 is the drawing illustrating the housing 16 that may be configured to accept canister 20, wherein canister 20 includes a medication to be dispensed via IMDD 14. Canister 20 may be replaceable or exchangeable such that IMDD 14 can accept a variety of different canisters containing any number of different medications. FIG. 6 to FIG. 8 show a flow of computing device screens representing the example of process for delivering sub-doses (pulses) of medication from a IMDD based on detected speech within the voice sensor (microphone). FIG. 9 is a conceptual drawing illustrating an example valve within a metered dose compartment of the IMDD, in steady state position when the dose of the content 100 is liquid and sealed in the canister when the releasing tunnel 111 not connected to the content 100, keeping the releasing pipe 101 empty. FIG. 10 is a conceptual drawing illustrating an example valve within a metered dose compartment of the IMDD, when the canister is pushed down, in opening position when the dose of the liquid content 100 is released via the releasing tunnel 111 that connected to the content 100, keeping the releasing pipe 101 full of the released content 100. FIG. 11 is a conceptual drawing illustrating an example when valve within a metered dose compartment of the IMDD is in close position, the canister is pulled up, and when the remaining of the dose of the liquid content 100 is sealed again, releasing tunnel 111 is disconnected from the content 100, keeping the releasing pipe 101 empty again.

In a method of the invention, a drug is transferred nearly directly to the brain, so that smaller doses can be used, minimizing potential systemic toxicity and precluding undesired great gradients of the therapeutic substance inside the body.

Because of the known limitation, the olfactory pathway as a conduit for transmission of drugs to the CNS have not been fully utilized so far. The invention provides in one embodiment a new means for handling one of the most painful medical problems of the Western world, Alzheimer's diseases which afflicts nearly everybody at certain age, usually appearing at the age of around 60 and, in an extrapolation, afflicting nearly everybody around the age of 120, practically appearing in more than 10% of people 65 and older in the U.S. The system of the invention may be employed for delivering medicaments in additional conditions afflicting the CNS, including dementias, depression, schizophrenia, headaches such as migraine or cluster headache, and other conditions which may be treated or prevented by a nasal spray.

While the invention has been described using some specific examples, many modifications and variations are possible. It is therefore understood that the invention is not intended to be limited in any way, other than by the scope of the appended claims.

The invention claimed is:

1. A device for delivering a dose of a medicament to a brain via ethmoid bone and olfactory mucosa of a subject, while bypassing a blood brain barrier without losses to airways and reducing peak systemic concentration of said medicament, comprising
   i) a canister for holding a solution or suspension of said medicament;
   ii) a voice sensor configured to generate an electrical signal within a portion of the device in response to a vocal signal, wherein said vocal signal is a speech of said subject;
   iii) a processor configured to receive said electrical signal as a command for starting a motor in response to the speech of said subject;
   iv) a valve associated with said motor and configured to release a part of said dose into nasal cavities of said subject when the motor is started, wherein the medicament is pumped from said canister in the form of solution or suspension and released into said cavities in the form of aerosol, said dose thus being delivered only in response to the subject's speech, said speech moving soft palate and naturally separating the nasal cavities of said subject from the airways, thereby limiting quantity of the medicament which enters to said airways; and v) an integrator for registering total quantity of the released medicament, of which dose is divided into a plurality of said parts;

wherein said peak systemic concentration is reduced because of a) said limiting quantity of the medicament entering the airways, and b) said dividing said dose into a plurality of said parts.

2. The device of claim 1, wherein said subject has lowered level of alertness or reduced cognitive abilities.

3. The device of claim 1, wherein said voice sensor is configured to generate an electrical signal within a portion of the device in response to a vocal signal which is a speech of attending personnel who either starts the motor when the release of the medicament is required or blocks the motor when the release of the medicament is not required.

4. The device of claim 1, further comprising a loudspeaker enabling the subject to hear attending personnel or family members who may affect said subject to give said speech and thus to generate said electrical signal as said command starting said motor.

5. The device of claim 1, wherein said processor further records the speech of said subject who responds to questions aimed at characterizing level of alertness or cognitive abilities of the subject.

6. The device of claim 5, wherein said processor provides cognitive parameters corresponding to reactions of said subject.

7. The device of claim 6, wherein a size of said dose or its parts are affected by the cognitive parameters provided by said processor.

8. The device according to claim 1, wherein said voice sensor comprises a smartphone which connects the subject with attending personnel or family members.

9. The device of claim 8, wherein said smartphone comprises GPS and enables to locate the subject.

10. The device of claim 1, wherein said medicament is a medicament for treating or preventing a condition selected from the group consisting of neurologic disorders, psychiatric disorders, and neurodegenerative disorders.

11. The device of claim 10, wherein said medicament is insulin and said neurodegenerative disorder is Alzheimer's disease.

12. The device of claim 1, further comprising nozzle tips for receiving from said valve said part of the dose and delivering said medicament into said cavities.

13. A method for delivering a dose of a medicament to a brain via ethmoid bone and olfactory mucosa of a subject, while both bypassing the blood brain barrier and reducing peak systemic concentration of said medicament, comprising i) generating by a voice sensor an electrical signal in response to a vocal signal wherein said vocal signal is a speech of said subject;

ii) processing said electrical signal by a processor;

iii) activating by said processor a motor associated with a valve configured to release one part of said dose, said dose being divided into a plurality of parts, into nasal cavities of said subject when the motor is started in response to the speech of said subject;

iv) releasing said one part of the dose in the form of aerosol, wherein said medicament is pumped from a canister where it is in the form of solution or suspension and is released into said cavities in the form of aerosol; and v) registering total quantity of the medicament released during certain period;

wherein peak systemic concentration of said medicament is reduced because a) said medicament passes through said nasal cavities via ethmoid bone and olfactory mucosa to the brain while said speech moves the soft palate of the subject, thereby naturally separating said nasal cavities from the airways and limits the quantity of the medicament which enters to the blood system of the subject, and b) said dose is divided into said plurality of said parts.

14. The method of claim 13, further comprising recording the speech of said subject when responding to questions aimed at characterizing the level of alertness or cognitive abilities of the subject.

15. The method of claim 13, wherein said subject has lowered level of alertness or cognitive abilities of the subject.

16. The method of claim 13, further comprising providing cognitive parameters of said subject.

17. The method of claim 13, wherein said sensor comprises a smartphone which connects the subject with attending personnel or family members.

18. The method of claim 17, further comprising locating the subject by a GPS associated with the smartphone.

19. The method of claim 13, wherein said substance is a medicament for treating or preventing a condition selected from the group consisting of neurologic disorders, psychiatric disorders, and neurodegenerative disorders.

20. The method of claim 19, wherein said condition limits the capabilities of the subject to fully cooperate during delivering said substance.

21. The method of claim 19, wherein said condition is Alzheimer's disease and said substance is insulin.

* * * * *